United States Patent [19]

Knudsen

[11] 4,233,143
[45] Nov. 11, 1980

[54] MEASURED VALUE RECEIVER FOR THE POLAROGRAPHIC MEASUREMENT OF GASES IN LIQUIDS

[75] Inventor: Ole F. Knudsen, Sonderborg, Denmark

[73] Assignee: Danfoss A/S, Nordborg, Denmark

[21] Appl. No.: 954,328

[22] Filed: Oct. 25, 1978

[30] Foreign Application Priority Data

Oct. 27, 1977 [DE] Fed. Rep. of Germany ....... 2748191

[51] Int. Cl.³ ..................... G01N 27/30; G01N 27/46
[52] U.S. Cl. ................................................ 204/195 P
[58] Field of Search ............................ 204/1 P, 195 P

[56] References Cited

U.S. PATENT DOCUMENTS

| | | | |
|---|---|---|---|
| 3,211,638 | 10/1965 | Halvorsen | 204/1 P |
| 3,334,623 | 8/1967 | Hillier et al. | 204/195 P |
| 3,351,544 | 11/1967 | Medlar | 204/195 P |
| 3,445,369 | 5/1969 | Porter et al. | 204/195 P |
| 3,454,485 | 7/1969 | Hauk et al. | 204/195 P |
| 3,510,421 | 5/1970 | Gealt | 204/195 P |
| 3,518,179 | 6/1970 | Bleak et al. | 204/195 P |
| 3,767,552 | 10/1973 | Lauer | 204/195 P |
| 3,785,947 | 1/1974 | Baldwin et al. | 204/195 P |
| 3,826,730 | 7/1974 | Watanabe et al. | 204/195 P |
| 3,948,746 | 4/1976 | Poole | 204/195 P |
| 3,997,419 | 12/1976 | Scott | 204/195 P |
| 4,100,048 | 7/1978 | Pompei et al. | 204/195 P |

FOREIGN PATENT DOCUMENTS 697764 11/1964 Canada .................. 204/195 P

*Primary Examiner*—G. L. Kaplan
*Attorney, Agent, or Firm*—Wayne B. Easton

[57] ABSTRACT

The invention relates to a measured value receiver for the polarographic measurement of gases in liquids. The unit comprises a main mounting member having an end face with associated cathode and anode contacts and a carrier member connectable thereto having an end face with cooperably engaging cathode and anode contacts. The carrier member has an annularly shaped wall and a central port member forming an annularly shaped chamber. A diaphragm permitting diffusion of gases covers the end faces of the wall and post member to enclose the chamber. A quantity of electrolyte completely fills the chamber but the diaphragm remains in contact with the post member. The post member extends a further distance outwardly than the surrounding wall so that the diaphragm assumes an inwardly and concavely formed contour. A main purpose of this construction is to make the receiver substantially insensitie to pressure fluctuations.

1 Claim, 2 Drawing Figures

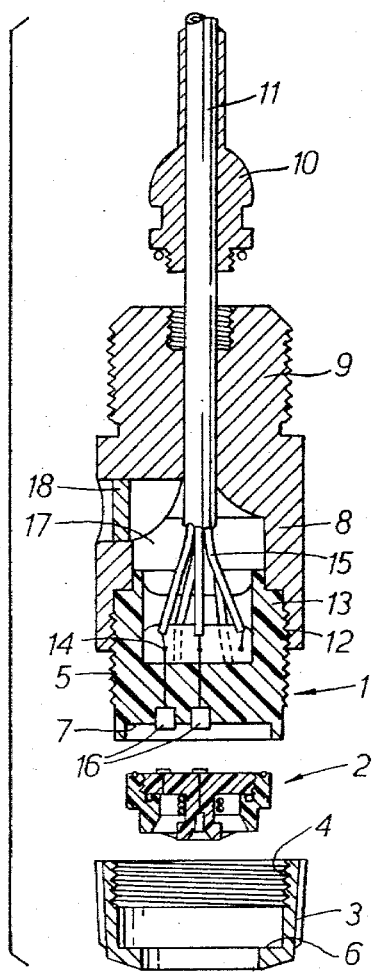
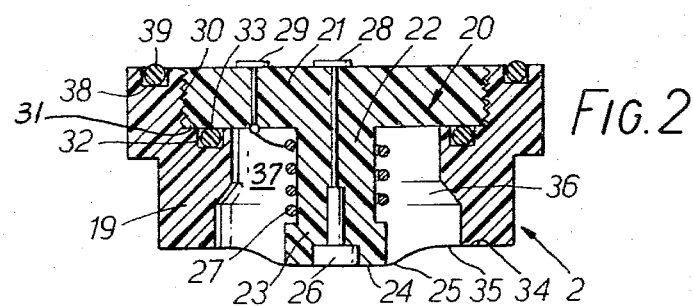

MEASURED VALUE RECEIVER FOR THE POLAROGRAPHIC MEASUREMENT OF GASES IN LIQUIDS

The invention relates to a measured value receiver for the polarographic measurement of gases, particularly oxygen, in liquids, comprising a mounting and a carrier replaceably secured thereto, wherein the end of the carrier comprises on a supporting face a cathode, a chamber filled with an electrolyte, and a diaphragm which covers the supporting face and electrolyte chamber, permits diffusion of gas, has an anode projecting into its interior and has a cathode connecting contact at its rear, particularly the electrolyte chamber possessing an annular groove surrounding the supporting face, the supporting face being proud of the remainder of the end face.

In such measured value receivers, the cathode forms a polarised electrode. When the liquid to which the diaphragm is subjected contains a gas which can diffuse through the diaphragm, depolarisation of the electrode is produced, leading to a flow of current which is a function of the partial pressure of the gas in the liquid.

In a known measured value receiver of this kind, the anode is carried by the mounting. It is eccentrically arranged and projects into a rear annular groove of the carrier that is closed by the mounting. This first annular groove is connected to an annular groove at the end by way of passages. Both annular grooves from an electrolyte chamber which is only partially filled with an electrolyte. To replace the diaphragm and the cathode, the carrier can be replaced by a similar new carrier. However, this requires great care so that the anode which freely projects from the mounting is not bent. In addition, this measured value receiver is very sensitive to pressure fluctuations. At elevated liquid pressures, the diaphragm is pushed deeply into the electrolyte chamber because the air cushion above the electrolyte is very compressible. Over-stretching occurs which brings about rapid aging of the diaphragm. When the pressure is relaxed, the diaphragm becomes slack and gas bubbles can accumulate between the supporting face and the diaphragm. Overall, considerable variations can occur in the spacing between the diaphragm and the cathode that should remain as constant as possible to achieve accurate measuring results.

In another known measured value receiver, the diaphragm is applied as a thin layer direct to the end face of a rigid porous body which carries at least the cathode and possibly also the anode therebeneath. The pores of this body, which may for example be of sintered glass, and the space therebehind are completely filled with the electrolyte. In this case the diaphragm is to a large extent protected against pressure deformations by the continuous support. However, temperature expansion of the electrolyte can lead to destruction or lifting off of the diaphragm. This construction involves a complicated method of production because a metal electrode must first be precipitated onto the porous body and subsequently the diaphragm is applied by cathode atomisation.

The invention is based on the problem of providing a cheaply made measured value receiver of the aforementioned kind which is substantially insensitive to pressure fluctuations.

This problem is solved according to the invention in that the amount of electrolyte is such that the electrolyte chamber is filled completely but the diaphragm has not yet lifted off the supporting face, and that the carrier also carries the anode and has an anode connecting contact at its rear.

In this construction, the electrolyte serves to support the diaphragm when the latter is subjected to a stronger pressure. The electrolyte is able to perform this function because it is substantially incompressible and completely fills out the electrolyte chamber. Since the carrier with electrolyte filling is replaceable, there is also no danger that, during replacement in situ, the wrong amount of electrolyte might be introduced, whereby the accuracy of measurement would suffer. The user need therefore not be concerned with either the electrolyte nor with the accurate dispensing of the quantity or cleaning and careful treatment of the anode.

It is particularly favourable if the amount of the electrolyte is such that the diaphragm curves somewhat inwardly in the region of the electrolyte chamber. With this feature one ensures that temperature expansion of the electrolyte will not cause the diaphragm to be lifted off the supporting face. The spacing of the diaphragm to be lifted off the supporting face. The spacing of the diaphragm from the cathode is therefore not only substantially independent of the pressure but it is also to a large extent independent of temperature.

It is also favourable if the supporting face proud of the remainder of the end face has a sharp peripheral edge. On the occurrence of pressure or temperature variations, only the part of the diaphragm between the sharp peripheral edge and the secured margin will deform; the part of the diaphragm disposed above the supporting face will retain its position practically without charge.

In a preferred embodiment, the carrier consists of two parts which bound the electrolyte chamber and contract it when put together, and provision is also made for a closable outlet for the excess electrolyte to leave the electrolyte chamber during contraction. One can then fill the electrolyte chamber with the electrolyte before the two carrier parts are assembled. During assembly, the excess electrolyte is then automatically expelled from the electrolyte chamber.

Preferably, it is ensured that the substantially rotationally symmetrical carrier consists of an annular outer member having the diaphragm secured to the front and an internal screwthread at the back, and an inner member having the supporting face on a head at the front and carrying an external screwthread on a plate at the back. For assembly, the outer and inner members are simply screwed into each other.

In this case, the outer member can have a step which adjoins the internal screwthread and against which the plate of the inner member abuts. This gives an electrolyte chamber of predetermined size.

An annular groove with an elastic O-ring may be provided in the step or plate. This O-ring serves as a closure which becomes effective when the electrolyte chamber has reached its final size.

In this connection it is favourable if the diaphragm is pressed into the electrolyte chamber from the outside during assembly of the two carrier parts. In this way it is permissible for the closure, such as the O-ring, already to become effective just before the two parts have reached their final position. Upon further assembly of the two parts, no further electrolyte can then be expelled; however, this quantity of electrolyte is taken up by a corresponding deformation of the prestressed diaphragm without the latter being lifted off the supporting face. Pressing the diaphragm inwardly also brings about the curvature desired to compensate temperature expansion. The pretensioning means may be an elastic support, e.g. a foam rubber member or the like, by which the diaphragm is pushed into the electrolyte chamber.

The screwthread can be sealed with putty at the outside. This can be done in addition to the O-ring seal or constitute the only seal. In addition, the putty securely fixes the two parts in their relative position.

The cathode can be inserted in the head as a rivet which is preferably guilded. The anode may be formed of a wire, preferably of silver, wound about a neck connecting the plate and head. In this way the two electrodes are accommodated in a comparatively small space but nevertheless well insulated from each other.

The anode and cathode connecting contacts may be disposed at the rear of the inner member and a further O-ring seal may be provided at the rear of the outer member. The seal becomes effective when the carrier is pressed against a supporting face of the mounting. This can for example be effected by means of a cap nut. In this construction the electrical elements are concentrated on the inner member and the sealing elements on the outer member.

The invention will now be described in more detail with reference to an example illustrated in the drawing, wherein:

FIG. 1 is a longitudinal section through a measured value receiver according to the invention with the parts shown in an exploded view and FIG. 2 is an enlarged representation of the carrier.

The measuring sensor shown in FIG. 1 comprises a mounting 1, a carrier 2 and a cap nut 3. When the latter is screwed with the aid of its internal screwthread 4 onto an external screwthread 5 of the mounting, the carrier 2 is retained between the step 6 of the cap nut 3 and the end face 7 of the mounting 1.

The mounting consists of a main portion 8 with a screwthreaded head 9 provided with a liquid-tight through connector 10 for a cable 11, and an insert 13 which is connected thereto by a screwthread 12 and is provided with electric connecting means 14 for connecting a plurality of leads 15 as well as two contact springs 16 disposed in the region of the end face 7 and connected to associated connecting means 14. The hollow interior chamber 17 is further closed by a plug 18. The additional leads 15 can for example serve as conductors extending to one or more thermistors which are in thermal contact with the contacts 16 so that the influence of the surrounding temperature can be compensated in the associated evaluating circuit.

The carrier 2 is shown to a larger scale in FIG. 2. It consists of an annular outer member 19 and an inner member 20 which consists of a plate 21, a neck 22 and a head 23. The latter forms a supporting face 24 at its end, this face being bounded by a sharp edge 25 and carrying in the middle a cathode 26 in the form of a guilded rivet. The anode 27 is in the form of a silver wire coil placed about the neck 22. At the rear of the plate 21 there is a cathode connecting contact 28 and an anode connecting contact 29. The plate 21 is connected to the outer ring 19 by way of a screwthread 30 and is screwed in until it abuts a step 31. In this step there is an annular groove 32 containing an O-ring seal 33. A diaphragm 35 which determines the diffusion and covers the supporting face 24 and thus also the cathode 26 is secured to the front end 34 of the outer ring 19. Between the outer member 19, inner member 20 and diaphragm 35 there is an electrolyte chamber 36 which is completely filled with an electrolyte 37. The amount of this electrolyte is such that the diaphragm 35 is curved inwardly between the end face 34 of the outer member 19 and the sharp edge 25 of the supporting face 24 which projects beyond this end face 34. The carrier 2 that is thus completed forms an operable capsule which is pushed against the mounting 1 by means of the cap nut 3, an O-ring seal 39 disposed in a groove 38 coming to lie against the end face 7 of the mounting and the connections 28 and 29 coming into contact with the contact spring 16. The measured value receiver is then ready for operation.

Manufacture of the replacement carrier 2 is effected as follows. The outer member 19 is produced with the diaphragm 25 secured thereto. The inner member 20 is produced with the cathode 26 and anode 27. The internal chamber of the outer member 19 is then filled with an electrolyte 37. The inner member 20 is thereupon screwed in, the diaphragm 35 being supported by an elastic support, e.g. of foam rubber. As the inner member is screwed in, excessive electrolyte is pushed outwardly by way of the screwthread 30 until the plate 21 sufficiently compresses the O-ring seal 33 to obtain a seal. However, this occurs only just before reaching the final position defined by abutment against the step 31. During this short movement, no further electrolyte can escape; instead, the diaphragm 35 is displaced but it can still exhibit inward curving because of the prestressing applied with the aid of the elastic support. Finally, the screwthread 30 is closed with putty, e.g. the plastics mastic marketed under the trade name 'Lock-tite'. The outer member 19 and inner member 20 are of insulating material, which may be extruded.

The completed measured value receiver can be used at the most varied depths of water. The rising pressure does not result in impermissible deformation of the diaphragm 35 because the latter is supported by the incompressible electrolyte 37 in the electrolyte chamber 36. Further, the measured value receiver can be used at very different temperatures. Contraction or expansion of the electrolyte 37 as a result of such a change in temperature merely leads to the diaphragm 35 becoming more or less curved. On the other hand, the conditions within the sharp edge 25 remain practically unchanged. In particular, the spacing between the diaphragm and cathode 26 stays substantially constant.

Instead of the cap nut 3, use can be made of a cap which is snapped onto the insert 13. It is also possible to form the connecting contact 28 by the head of a throughgoing solid rivet or pin of which the shank is cemented in a smooth hole and the end face forming the cathode is precision ground and subsequently guilded.

What is claimed is:

1. A measured value receiver for the polarograph measurement of gases in liquids, comprising a mounting member having an end face with associated cathode and anode contacts, carrier means having a base with a face in abutting engagement with said end face, means for connecting said carrier means to said mounting member, said carrier means having an annularly shaped wall and a central post member extending from said base and forming an annularly shaped recess, said wall having an end face and said post member having a supporting face disposed a greater distance from said base than said end face, said post supporting face having a cathode associated therewith, said carrier means having an anode projecting into said chamber, said cathode and anode having corresponding contacts in said base face cooperable with said like contacts in said mounting member end face, a diaphragm permitting diffusion of gas attached to said wall end face to enclose said recess to form a completely fluid tight chamber, and a quantity of electrolyte filling said chamber with said quantity being selected so that said diaphragm is in contact with said supporting face and has an inwardly and concavely formed contour to allow for temperature responsive expansion and contraction of said electrolyte.

* * * * *